(12) United States Patent
Kim et al.

(10) Patent No.: US 10,543,248 B2
(45) Date of Patent: Jan. 28, 2020

(54) PHARMACEUTICAL COMPOSITION HAVING PREVENTATIVE OR TREATMENT EFFECT ON INFLAMMATORY BOWEL DISEASES COMPRISING STEMONAE RADIX EXTRACT

(71) Applicant: University-Industry Cooperation Group of Kyung Hee University, Gyeonggi-do (KR)

(72) Inventors: Jin Ju Kim, Gyeonggi-do (KR); Eun Jung Ko, Seoul (KR); Eui Jeoung Lee, Seoul (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 681 days.

(21) Appl. No.: 14/412,178

(22) PCT Filed: Jul. 3, 2013

(86) PCT No.: PCT/KR2013/005893
§ 371 (c)(1),
(2) Date: Dec. 30, 2014

(87) PCT Pub. No.: WO2014/007537
PCT Pub. Date: Jan. 9, 2014

(65) Prior Publication Data
US 2015/0150934 A1 Jun. 4, 2015

(30) Foreign Application Priority Data
Jul. 3, 2012 (KR) ........................ 10-2012-0072394

(51) Int. Cl.
*A61K 36/904* (2006.01)
*A61K 36/00* (2006.01)

(52) U.S. Cl.
CPC ...... *A61K 36/904* (2013.01); *A61K 2236/331* (2013.01)

(58) Field of Classification Search
None
See application file for complete search history.

(56) References Cited

U.S. PATENT DOCUMENTS 7,871,631 B2 * 1/2011 Matsumoto .......... A61K 31/047
424/278.1
2013/0302844 A1 * 11/2013 Ikegami ............... A23C 9/1238
435/29

FOREIGN PATENT DOCUMENTS

| CN | 101972338 A | * | 2/2011 |
|---|---|---|---|
| CN | 101972338 A | * | 2/2011 |
| JP | 2007-126368 | | 5/2007 |
| KR | 10-2005-0004354 | | 1/2006 |
| KR | 2007072023 A | * | 7/2007 |
| KR | 10-2010-0103999 | | 9/2010 |

OTHER PUBLICATIONS

Heo, et al., "Baekbugeun immune suppression and asthma control effect of acupuncture on experimental study", Journal of Physiology and Pathology, 2006, vol. 20, No. 3, pp. 609-616.
Naver café, "Diarrhea, bloody stools and ulcerative colitis. 'Crohn's' disease. treatment", Sep. 2, 2008 (http://cafe.naver.com/ock629/304).

* cited by examiner

*Primary Examiner* — Michael Barker
*Assistant Examiner* — Randall Winston
(74) *Attorney, Agent, or Firm* — Cesari and McKenna, LLP

(57) ABSTRACT

The present invention relates to a pharmaceutical composition, which comprises a Stemonae Radix extract, for preventing or treating the occurrence of inflammatory bowel diseases due to cigarette smoke, a method for preventing or treating the occurrence of inflammatory bowel diseases using the composition, a method for suppressing the expression of inflammatory cytokines using the composition, and to a food composition, which comprises the Stemonae Radix extract, for preventing or treating the occurrence of inflammatory bowel diseases due to cigarette smoke. The pharmaceutical composition comprising the Stemonae Radix extract, according to the present invention, reduces the level of MMP12 expression that is known to destroy IL-1β, TNF-α, and IL-6, which are inflammatory cytokines that accompany the inflammatory bowel diseases, and elastin and collagen, and can suppress decrease in the number of lactobacilli in the intestine, and thus can be widely used in developing a safe and effective inflammatory bowel diseases treating agent.

3 Claims, 12 Drawing Sheets

[FIG. 1]
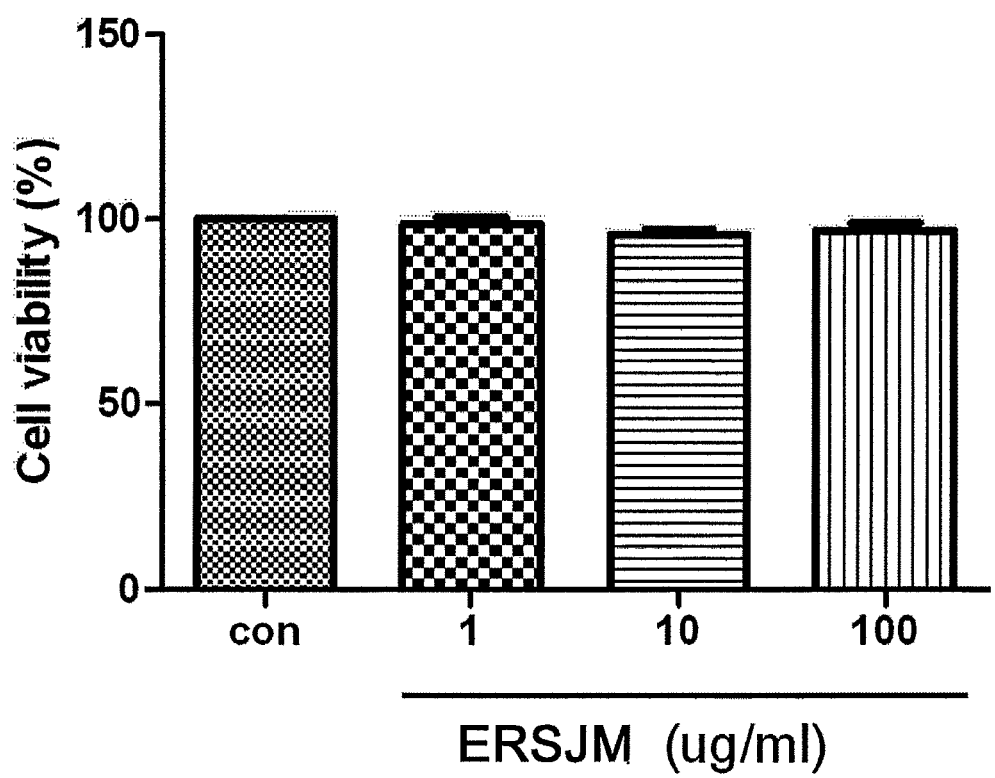

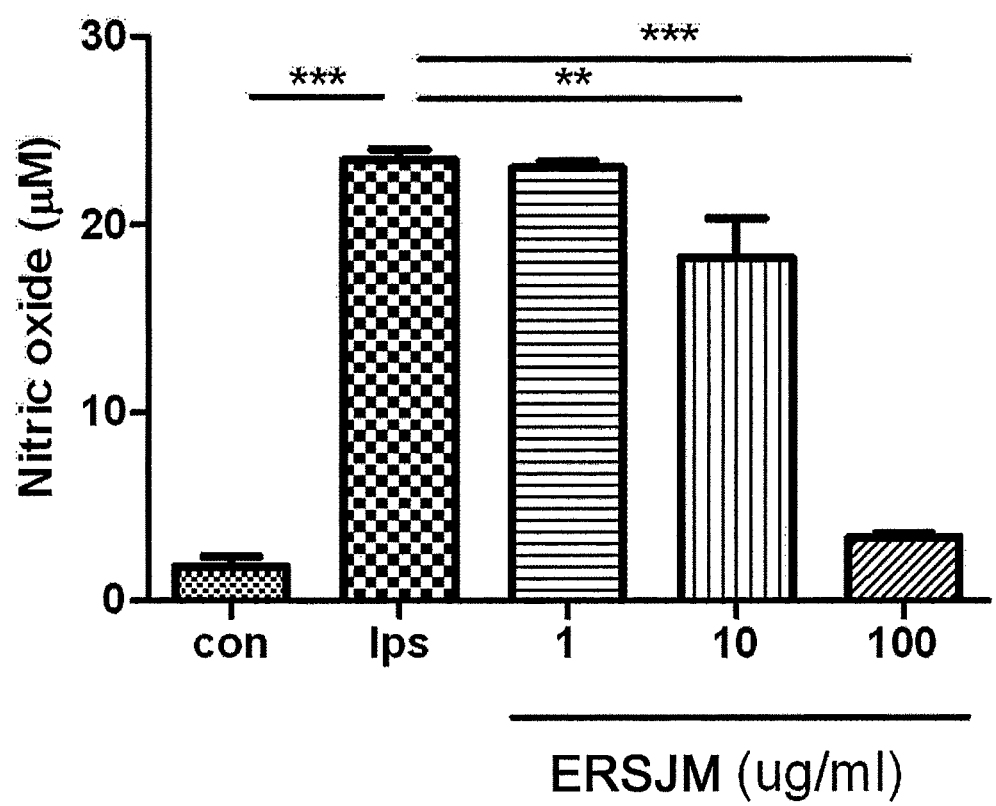
[FIG. 2]

[FIG. 3A]
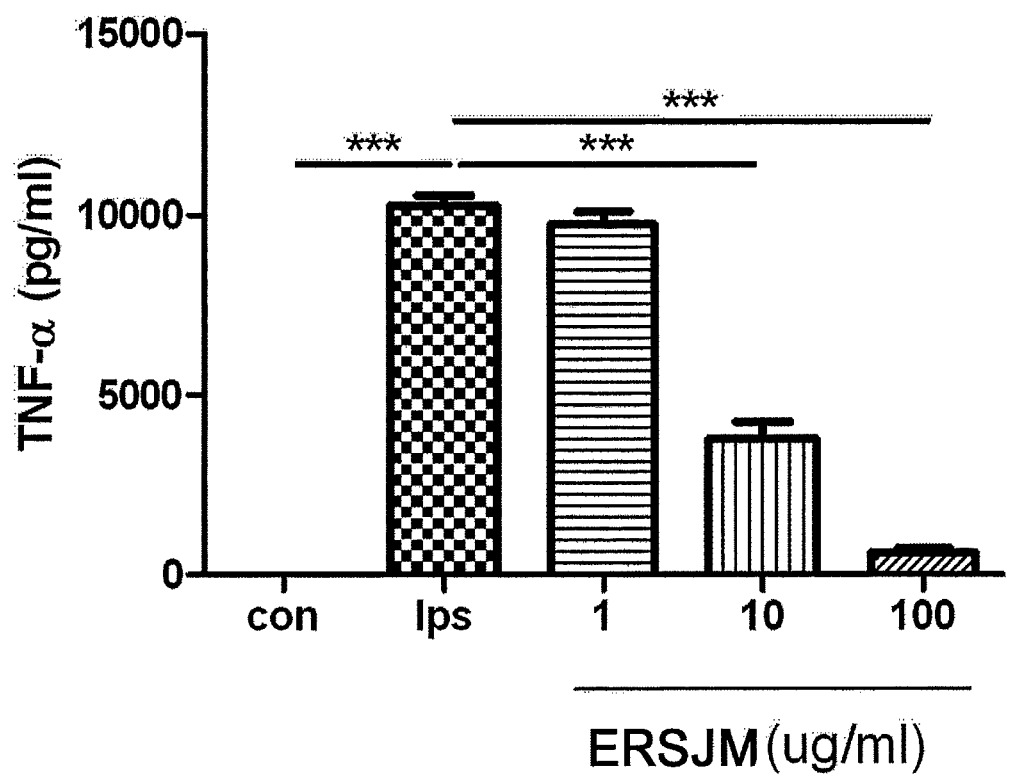

[FIG. 3B]
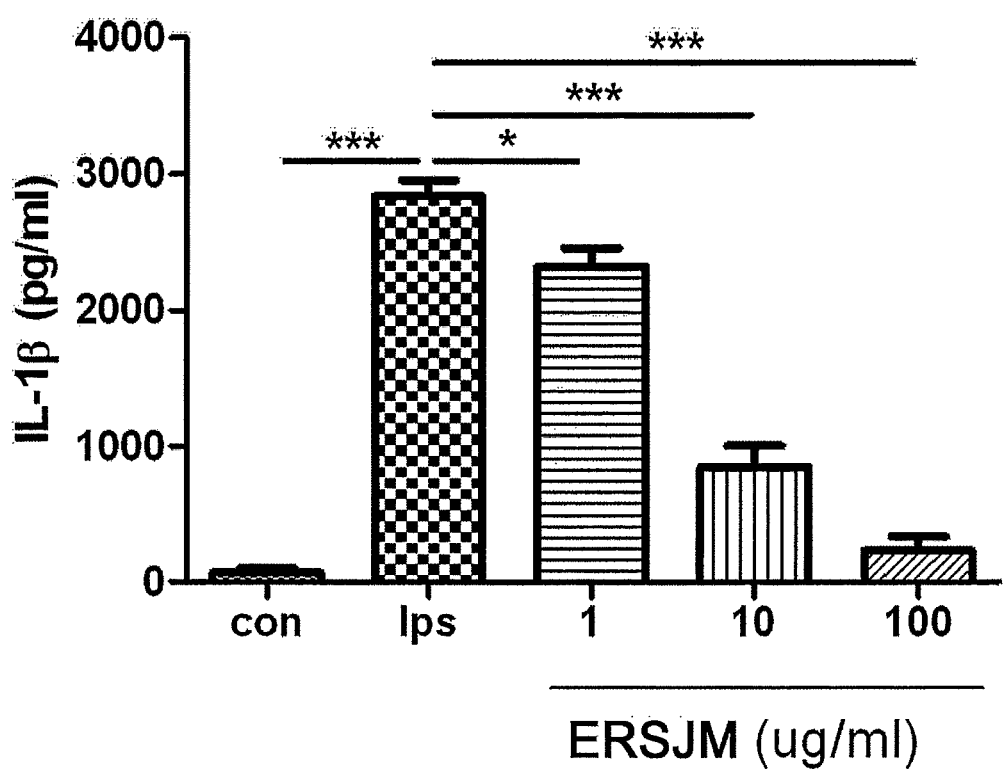

[FIG. 3C]
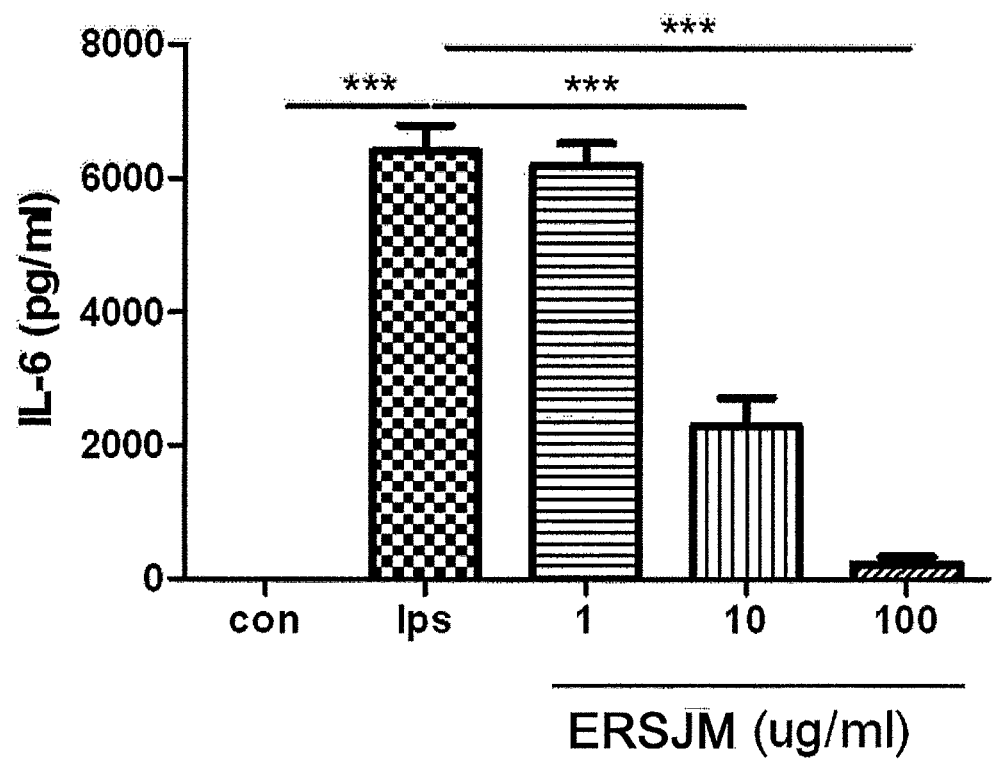

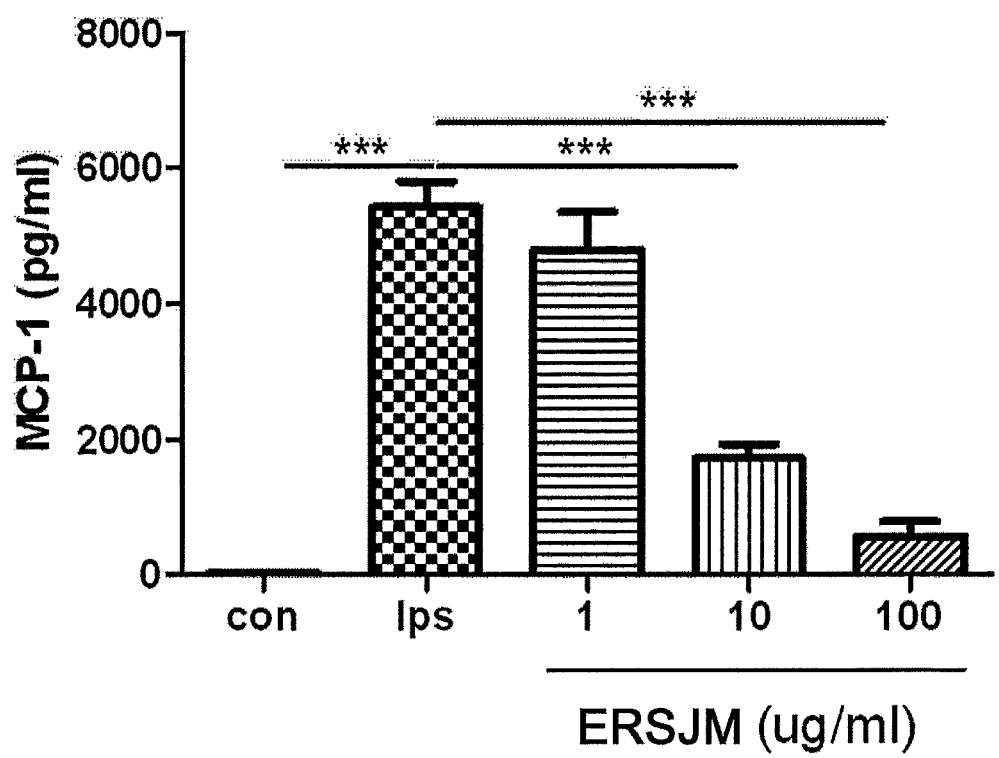
[FIG. 3D]

[FIG. 4A]
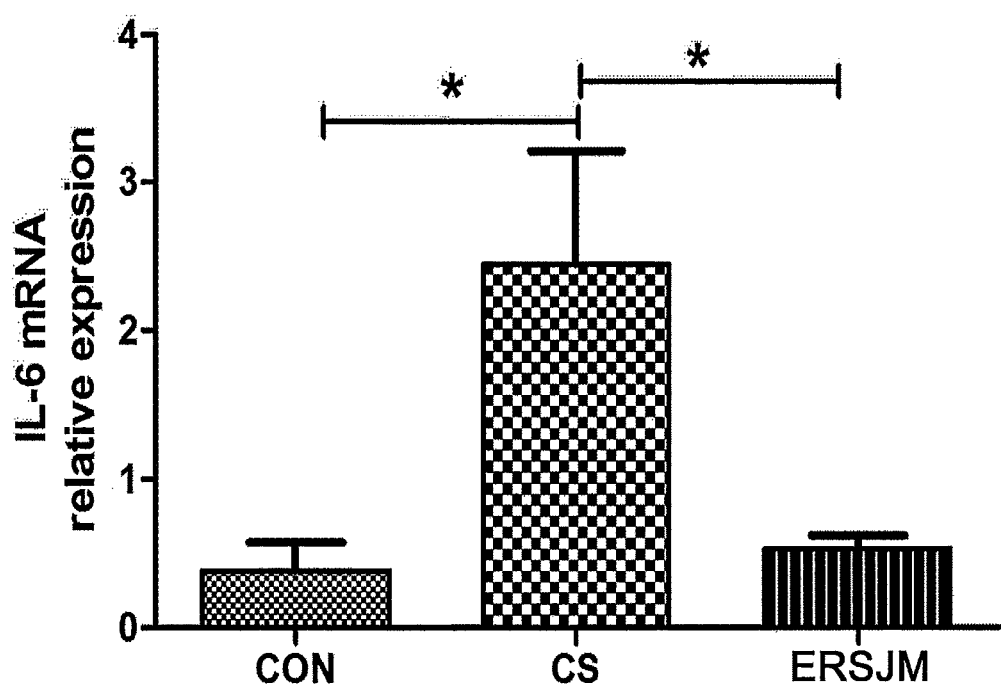

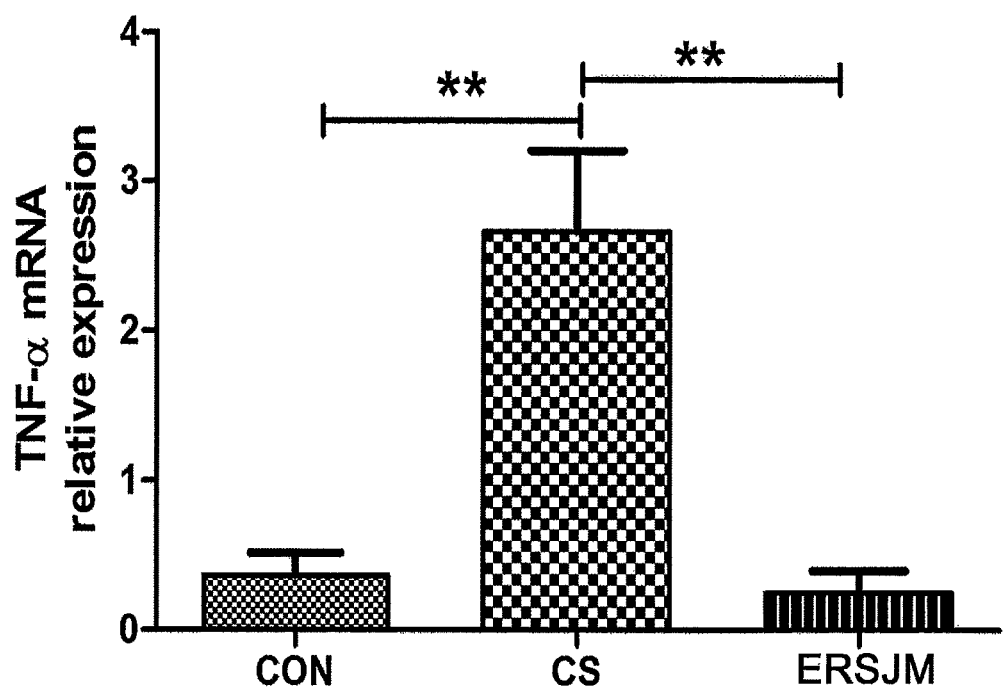
[FIG. 4B]

[FIG. 4C]
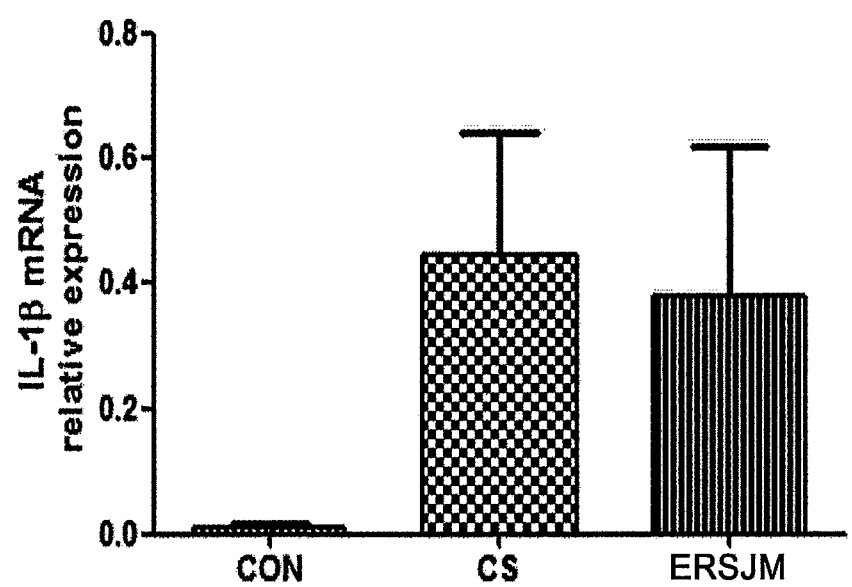

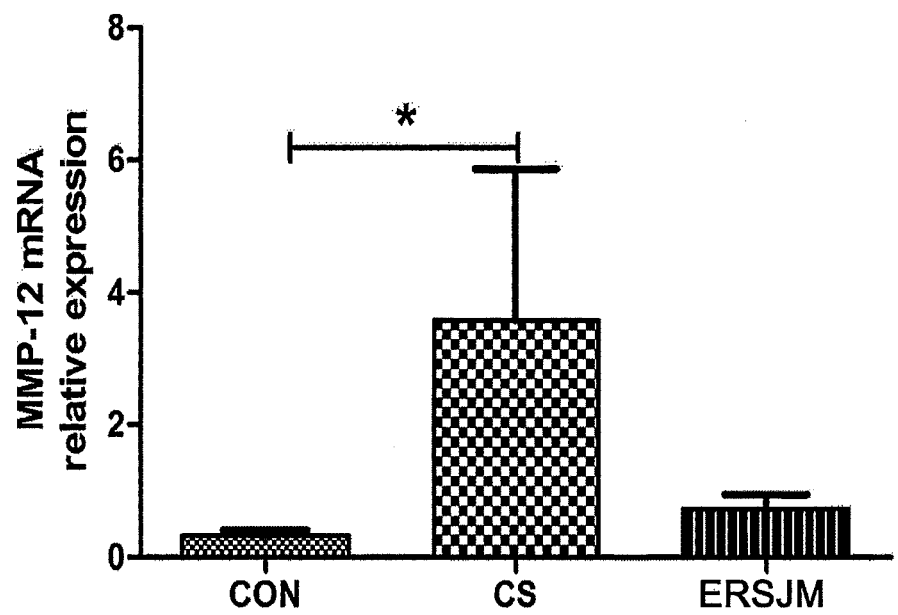
[FIG. 4D]

[FIG. 5]
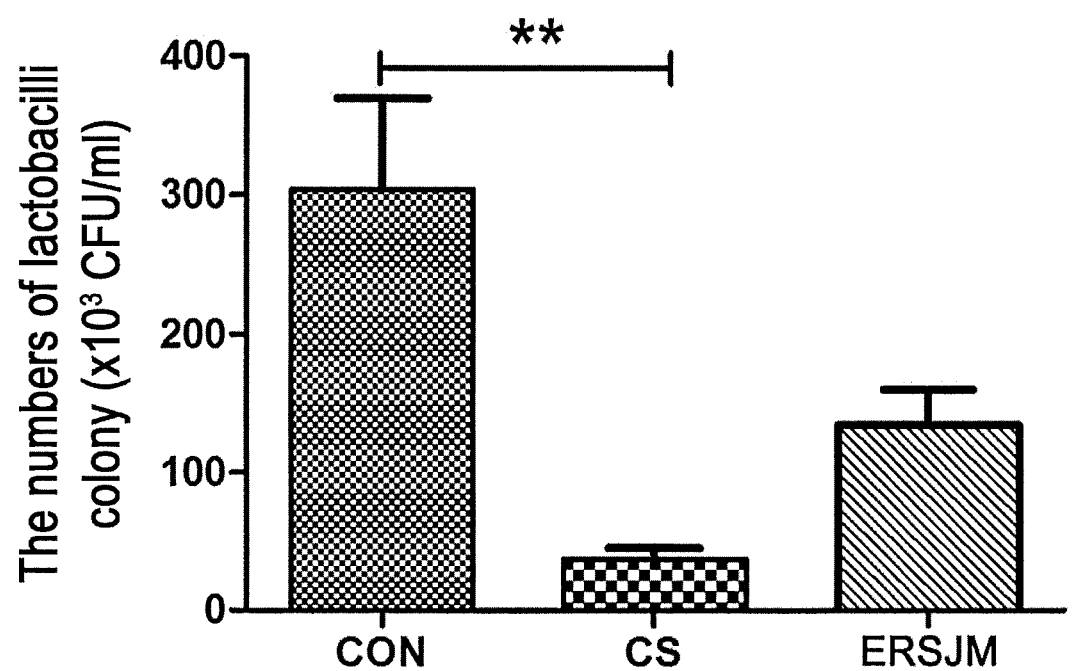

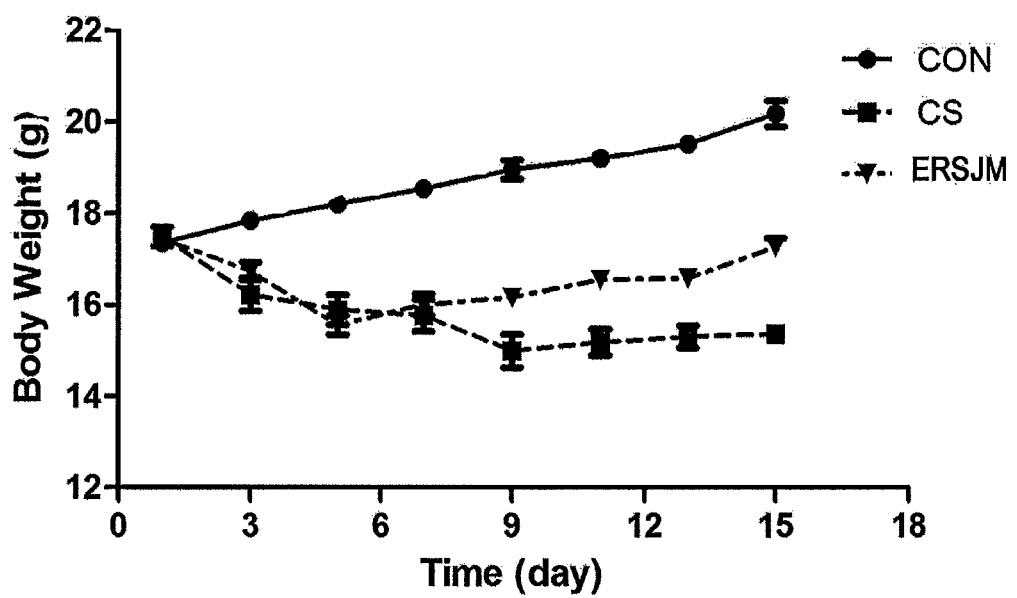
[FIG. 6]

PHARMACEUTICAL COMPOSITION HAVING PREVENTATIVE OR TREATMENT EFFECT ON INFLAMMATORY BOWEL DISEASES COMPRISING STEMONAE RADIX EXTRACT

CROSS REFERENCE TO RELATED APPLICATIONS

This application is the National Stage of International Application No. PCT/KR2013/005893, filed on Jul. 3, 2013, which claims the benefit of Korean Application No. 10-2012-0072394, filed on Jul. 3, 2012. The contents of both applications are hereby incorporated by reference in their entirety.

BACKGROUND OF THE INVENTION

1. Field of the Invention

The present invention relates generally to a pharmaceutical composition for preventing or treating inflammatory bowel diseases comprising Stemonae Radix, and more particularly, to a pharmaceutical composition comprising a Stemonae Radix extract, which can prevent the development of inflammatory bowel diseases due to cigarette smoke, a method for preventing or treating inflammatory bowel diseases using the pharmaceutical composition, a method for inhibiting overexpression of inflammatory cytokines using the pharmaceutical composition, and a food composition comprising a Stemonae Radix extract, which can prevent or ameliorate the development of inflammatory bowel diseases due to cigarette smoke.

2. Description of the Related Art

As is well known in the art, inflammatory bowel diseases (IBD), which generally begin to develop in adolescent years, cause chronic inflammation in the gastrointestinal tract and are accompanied by symptoms such as abdominal pain, fever, diarrhea, and melena. Inflammatory bowel diseases are generally divided into two types: ulcerative colitis (UC) and Crohn's disease (CD). Ulcerative colitis is a type of diffuse nonspecific inflammation of an unknown cause occurring in colon, which mostly invades mucous membranes, frequently causes decay or ulcers and is accompanied by various systemic symptoms including bloody diarrhea, whereas Crohn's disease is a type of granulomatous inflammation of an unknown cause that develops ulcer, fibrosis, stenosis, and lesions in the entire digestive system from mouth to anus, and is accompanied by systemic symptoms such as abdominal pain, chronic diarrhea, fever, and malnutrition.

Although the exact cause of inflammatory bowel diseases has not been identified, allegedly they appear to occur due to a disorder in immune functions, in which factors such as innate immunity, production of cytokines, activation of CD4, etc., are known to be involved. In particular, cytokines are known to play an important role therein, and significantly increased levels of tumor necrosis cytokine (TNF-α), interleukin (IL)-1, IL-6, and IL-8 were observed in inflammatory lesions of the patients with ulcerative colitis or Crohn's disease.

Examples of drugs used for treating the inflammatory bowel diseases include steroid immunosuppressive agents, 5-aminosalicylic acid (5-ASA)-based drugs that block the production of prostaglandins (e.g., sulfasalazine), mesalazine, etc. However, they have little therapeutic effects and also cause serious side effects such as headaches, rashes, liver diseases, leucopenia, male infertility, etc., thus limiting the use of these drugs.

In this regard, the development of a therapeutic drug for treating the inflammatory bowel diseases without side effects will be very useful for safely and effectively treating patients with the diseases, but the development of the therapeutic drug has not yet been accomplished.

SUMMARY OF TILE INVENTION

The inventors of the present invention, while endeavoring to develop a therapeutic agent without side effects derived from a natural substance, discovered that a composition comprising a Stemonae Radix extract can inhibit the expression of MMP12, which is known to destroy inflammatory cytokines, elastin, and collagen, and can suppress the decrease in the number of lactobacilli in the intestine and thus can be used for treating inflammatory bowel diseases, thereby completing the present invention.

Accordingly, the present invention has been made keeping in mind the above problems occurring in the prior art, and an objective of the present invention is to provide a pharmaceutical composition comprising a Stemonae Radix extract for preventing or treating inflammatory bowel diseases.

Another objective of the present invention is to provide a method for preventing or treating inflammatory bowel diseases using the pharmaceutical composition.

A further objective of the present invention is to provide a method for inhibiting the expression of inflammatory cytokines using the pharmaceutical composition.

A still further objective of the present invention is to provide a food composition comprising a Stemonae Radix extract for preventing or ameliorating inflammatory bowel diseases.

Advantageous Effects of the Invention

The pharmaceutical composition of the present invention comprising a Stemonae Radix extract can reduce the expression level of MMP12, which is known to destroy inflammatory cytokines such as IL-1β, TNF-α, and IL-6, elastin, and collagen, accompanied with the inflammatory bowel diseases, and also can suppress the decrease in the number of lactobacilli in the intestine, thus being very useful in the development of a safe and effective therapeutic agent for treating inflammatory bowel diseases.

BRIEF DESCRIPTION OF THE DRAWINGS

The above and other objectives, features and other advantages of the present invention will be more clearly understood from the following detailed description taken in conjunction with the accompanying drawings, in which:

FIG. 1 is a graph illustrating the evaluation result of cell toxicities of Stemonae Radix extracts;

FIG. 2 is a graph illustrating the evaluation result of the effect of Stemonae Radix extracts on NO production;

FIG. 3A is a graph illustrating the evaluation result of the effect of Stemonae Radix extracts on TNF-α production;

FIG. 3B is a graph illustrating the evaluation result of the effect of Stemonae Radix extracts on IL-1β production;

FIG. 3C is a graph illustrating the evaluation result of the effect of Stemonae Radix extracts on IL-6 production;

FIG. 3D is a graph illustrating the evaluation result of the effect of Stemonae Radix extracts on MCP-1 production;

FIG. 4A is a graph illustrating the change in the level of IL-6 mRNA by the treatment of a Stemonae Radix extract of the present invention;

FIG. 4B is a graph illustrating the change in the level of TNF-α mRNA by the treatment of a Stemonae Radix extract of the present invention;

FIG. 4C is a graph illustrating the change in the level of IL-1β mRNA by the treatment of a Stemonae Radix extract of the present invention;

FIG. 4D is a graph illustrating the change in the level of MMP12 mRNA by the treatment of a Stemonae Radix extract of the present invention;

FIG. 5 is a graph illustrating the change in the number of lactobacilli by the treatment of a Stemonae Radix extract; and FIG. 6 is a graph illustrating the change in the body weight of mice by the treatment of a Stemonae Radix extract.

DESCRIPTION OF TILE PREFERRED EMBODIMENTS

In an aspect of the present invention to accomplish the above objectives, the present invention provides a pharmaceutical composition for preventing or treating inflammatory bowel diseases comprising a Stemonae Radix extract.

The present inventors, while performing studies to develop a therapeutic agent derived from a natural substance without side effects for treating inflammatory bowel diseases using various extracts of natural substances, had their attention drawn to the Stemonae Radix extract. As a result, they discovered that the Stemonae Radix extract can inhibit the production of nitric oxide (NO), caused by LPS treatment in a concentration-dependent manner, and also inhibit the production of various inflammatory cytokines in a concentration-dependent manner, without exhibiting any toxicity to the RAW 264.7 cell line derived from murine macrophages. Additionally, they also discovered that the Stemonae Radix extract can reduce the amount of expression of MMP12, which is known to destroy inflammatory cytokines, elastin, and collagen, the levels of which are increased with the onset of inflammatory bowel diseases, which were induced in mice by their exposure to cigarette smoke, and can also inhibit the decrease in the number of lactobacilli in the intestine and inhibit the decrease in body weight due to the inflammatory bowel diseases. Accordingly, the Stemonae Radix extract of the present invention can be used as an active ingredient of a pharmaceutical composition for preventing or treating inflammatory bowel diseases.

As used herein, the term "Stemonae Radix (root of *Stemona japonica* Miguel)" refers to a tuberous root of *Stemona japonica* Miguel or of a plant of the same species, which, morphologically, is straight or a little bent as a waterproof-type, is thin at both ends, has a yellow-white wrinkled outer surface, and irregular vertical wrinkles. It is hard and easily broken, its broken surface is keratinous and white, and its skin is contracted to its center and yellow. Its pharmacological actions include an antitussive action, an expectorating action, an insecticidal action, an antibacterial action, etc. In the herbal medicine art, it has therapeutic effects on the treatment of severe coughs, colds, coughs, and pertussis resulteing from tuberculosis, has a hemostatic action, an insecticidal action, and has been used for treating hives, dermatitis, scabies, etc.

As used herein, the term "Stemonae Radix extract" refers to an extract obtained by extracting the "Stemonae Radix" using water or an organic solvent.

The Stemonae Radix extract of the present invention may be used as an active ingredient of a composition for preventing, treating or ameliorating inflammatory bowel diseases. Preferably, the Stemonae Radix extract may be obtained using an extraction solvent such as water, a C1~C6 alcohol, hexane, chloroform, methyl acetate, butanol, etc., and more preferably the extraction solvent is water, a C1~C6 alcohol, or a combination thereof and most preferably, hot water or 70% ethanol extract of Stemonae Radix.

As used herein, the term "inflammatory bowel disease (IBD)" refers to a disease that induces an inflammation in the gastrointestinal tract with accompanying symptoms such as abdominal pain, fever, diarrhea, and melena. Inflammatory bowel diseases are generally divided into two types: ulcerative colitis (UC) and Crohn's disease (CD). Ulcerative colitis is a type of diffuse nonspecific inflammation of an unknown cause occurring in the colon, which mostly invades mucous membranes, frequently causes decay or ulcers and is accompanied by various systemic symptoms including bloody diarrhea, whereas Crohn's disease is a type of granulomatous inflammation of an unknown cause that develops ulcer, fibrosis, stenosis, and lesions in the entire digestive system from mouth to anus, and accompanies systemic symptoms such as abdominal pain, chronic diarrhea, fever, and malnutrition.

As used herein, the term "prevention" refers to all kinds of activities associated with the inhibition or delay of inflammatory bowel diseases by administering the pharmaceutical composition of the present invention.

As used herein, the term "treatment" refers to all kinds of activities associated with clinical intervention for the purpose of changing the natural process(es) of an individual or a cell to be treated, which may be performed while the clinical pathological state is still in progress or to prevent the occurrence of the same. Examples of the aimed purposes of the therapeutic effects may include preventing occurrence or recurrence of a given disease, alleviating the symptoms therefrom, reducing all the direct or indirect pathological results due to the disease, preventing metastasis, decreasing the progress of the disease, reducing or temporarily alleviating and ameliorating the disease, or improving prognosis of the disease.

In the present invention, preferably, the above treatment should be understood as treating inflammatory bowel diseases using the pharmaceutical composition comprising the Stemonae Radix extract of the present invention.

In an embodiment of the present invention, a Stemonae Radix extract was obtained by extracting Stemonae Radix using water (Example 1-1), and the RAW 264.7 cell line treated with the Stemonae Radix extract was treated with LPS, and the levels of NO and various inflammatory cytokines produced in the cell line were measured. As a result, the Stemonae Radix extract did not show any cell toxicity against the RAW 264.7 cell line (FIG. 1), reduced the level of NO in a concentration-dependent manner (FIG. 2), and also reduced the levels of various inflammatory cytokines produced by LPS treatment in a concentration-dependent manner (FIGS. 3A through 3D). Additionally, when the mice orally administered with the Stemonae Radix extract were exposed to cigarette smoke, the mice showed alleviation of the symptoms of the inflammatory bowel disease(s) caused by the cigarette smoke (FIGS. 4A through 4D), a decrease in the number of lactobacilli in the intestine caused by the inflammatory bowel disease(s) (FIG. 5), and also a decrease in body weight caused by the inflammatory bowel disease(s) (FIG. 6).

Meanwhile, the pharmaceutical composition of the present invention may further include a suitable carrier, an excipient, or a diluent, conventionally used in the manufacture of a pharmaceutical composition. Specifically, the pharmaceutical composition may be prepared in the form of oral formulations such as powders, granules, tablets, capsules, suspensions, emulsions, syrups, and aerosols, external use formulations, suppositories, and sterile injection solutions, according to the conventional methods. In the present invention, examples of the carrier, the excipient, or the diluent to be included in the pharmaceutical composition are lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and base oil.

For formulations, a commonly used filler, extender, binder, humectant, disintegrant, surfactant, diluent, or excipient may be added. Examples of the solid formulations for oral administration are tablets, pills, powders, granules, capsules, etc., and the formulations are prepared by mixing at least one excipient, e.g., starch, calcium carbonate, sucrose or lactose, gelatin, etc., with the extract or fractions thereof. Additionally, lubricants such as magnesium stearate and talc may be used in addition to the simple excipients. Examples of liquid formulations for oral administration are suspensions, internal-use liquid medicines, emulsions, syrups, etc., and various excipients, e.g., humectants, sweeteners, fragrant, preservatives, etc., may be added in addition to the simple diluents such as water and liquid paraffin. Examples of formulations for parenteral administration are sterile aqueous solutions, non-aqueous solvents, suspensions, emulsions, lyophilized formulations, and suppositories. Examples of the non-aqueous solvents and suspensions may include propylene glycol, polyethylene glycol, a vegetable oil such as olive oil, injectable ester such as ethyl oleate, etc. Examples of the bases for the suppositories may include witepsol, macrogol, tween 61, cacao butter, laurinum, glycerogelatin, etc.

In an embodiment of the present invention, the amount of the Stemonae Radix extract contained in the pharmaceutical composition according to an embodiment of the present invention may be in the range from 0.0001 wt % to 50 wt % relative to the total weight of the final composition, and more preferably, 0.01 wt % to 10 wt %, although it is not particularly limited thereto.

The pharmaceutical composition of the present invention may be administered in a pharmaceutically effective amount. As used herein, "a pharmaceutically effective amount" refers to an amount sufficient for the treatment of diseases at a reasonable benefit/risk ratio applicable to a medical treatment, and the level of the effective dose may be determined by factors including severity of illness, drug activity, age, body weight, health conditions, drug sensitivity of a subject, administration time, administration route and dissolution rate, length of treatment of the pharmaceutical composition of the present invention, drug(s) used in combination with or simultaneously with the pharmaceutical composition of the present invention, and other factors well known in the medical field. The pharmaceutical composition of the present invention may be administered as an individual therapeutic agent or in combination with other therapeutic agent(s), and also sequentially or simultaneously with the conventional therapeutic agent(s). Additionally, the pharmaceutical composition of the present invention may be administered as a single dose or in multiple divided doses. Additionally, it is important that the least amount which can achieve the maximum effect without any side effects be administered in consideration of all the factors described above.

The dose of the pharmaceutical composition of the present invention may be determined by a skilled person in the art considering the intended use(s), addiction level of disease(s), age, body weight, sex and anamnesis of a subject, or the kinds of ingredients used as active ingredient(s), etc. For example, the pharmaceutical composition comprising the Stemonae Radix extract of the present invention may be administered in the range of from about 1 mg/kg/day to about 20 mg/kg/day for mammals including humans, and preferably from 1 mg/kg/day to 10 mg/kg/day. The pharmaceutical composition of the present invention may be administered once daily or in a few divided doses, although not particularly limited thereto.

In another aspect of the present invention to achieve the objectives, there is provided a method for preventing or treating inflammatory bowel diseases including administering a pharmaceutically effective amount of the pharmaceutical composition comprising the Stemonae Radix extract of the present invention as an active ingredient to a subject having a risk of developing an inflammatory bowel disease or having the inflammatory bowel disease.

As described above, the Stemonae Radix extract of the present invention can be used as an active ingredient of the pharmaceutical composition for preventing or treating inflammatory bowel diseases, and it thus can be used for preventing or treating inflammatory bowel diseases.

As used herein, the term "subject" refers to all kinds of animals including humans having a risk of inflammatory bowel disease(s) or having inflammatory bowel disease(s). The administration of the pharmaceutical composition of the present invention can alleviate or treat the inflammatory bowel disease(s) of the subject.

As used herein, the term "alleviation" refers to all kinds of activities associated with ameliorating or advantageously changing the status of inflammatory bowel disease(s) by the administration of the pharmaceutical composition of the present invention.

As used herein, the term "administration" refers to an activity of introducing the pharmaceutical composition of the present invention to a subject by an appropriate method, and the pharmaceutical composition may be administered via various routes of oral or parenteral routes as long as they can deliver the same to the target tissues.

Regarding the method for treating inflammatory bowel diseases, the pharmaceutical composition may be administered via any general routes as long as they can deliver the same to the target tissues. According to the intended purposes, the pharmaceutical composition of the present invention may be administered via intraperitoneal administration, intravenous administration, intramuscular administration, subcutaneous administration, intracutaneous administration, oral administration, intranasal administration, intrapulmonary administration, and intrarectal administration, although not particularly limited thereto. Additionally, the pharmaceutical composition may be administered via any apparatus that enables to transport the active ingredient to a target cell.

In a further aspect of the present invention to achieve the objectives, there is provided a food composition for preventing or ameliorating inflammatory bowel diseases comprising the Stemonae Radix extract of the present invention.

The Stemonae Radix has long been used as a herbal raw material and its safety has been approved accordingly. Therefore, it can be used as a food composition.

The Stemonae Radix extract of the present invention may be included in the range from 0.01 wt % to 100 wt % relative to the total weight of the food composition, preferably from 1 wt % to 80 wt %. When the food is a beverage it may be included in the range from 1 g to 30 g per 100 mL of the food composition, preferably from 3 g to 20 g. Additionally, the composition may further include additional ingredients which may be conventionally used in food compositions to improve smell, taste, sight, etc., e.g., vitamins A, C, D, E, B1, B2, B6, B12, niacin, biotin, folate, panthotenic acid, etc. Additionally, the composition may further include minerals such as Zn, Fe, Ca, Cr, Mg, Mn, Cu, etc. Additionally, the composition may further include amino acids such as lysine, tryptophan, cysteine, valine, etc. Additionally, the composition may further include food additives such as preservatives (potassium sorbate, sodium benzoate, salicylic acid, dehydro sodium acetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vaniline, lactones, etc.), swelling agents (alum, potassium D-hydrogn tartate, etc.), fortifiers, emulsifiers, thickners (adhesive pastes), film-forming agents, gum base agents, antifoaming agents, solvents, improvers, etc. The food additives may be selected according to the food kinds and used in an appropriate amount.

Additionally, functional foods for preventing or ameliorating inflammatory bowel diseases may be manufactured using the food composition comprising the Stemonae Radix.

Specifically, processed foods having a good shelf-life with a modified property of agricultural products, livestock products, or marine products applied thereto, may be manufactured using the food composition. Examples of the processed foods may include cookies, beverages, alcoholic beverages, fermented foods, canned foods, milk-processed foods, meat-processed foods, noodles, etc. Examples of the cookies include biscuits, pies, cakes, breads, candies, jellies, gums, cereals (meal substitutes such as grain flakes). Examples of the beverages include carbonated soft drinks, functional isotonic drinks, juices (e.g., apple-, pear-, grape-, aloe-, tangerine-, peach-, carrot-, tomato juices, etc.), sweet rice drinks, etc. Examples of the alcoholic beverages include refined rice wine, whisky, soju (Korean distilled spirits), beer, liquors, fruits wine, etc. Examples of the fermented foods include soy sauce, bean paste, red pepper paste, etc. Examples of the canned foods include seafood canned foods (e.g., canned tuna, mackerel, mackerel pike, conch, etc.), livestock canned foods (canned beef, pork, chicken, turkey, etc.), agricultural canned foods (canned corn, peach, pineapple, etc.). Examples of milk-processed foods include cheese, butter, yogurt, etc. Examples of meat-processed foods include pork cutlets, beef cutlets, chicken cutlets, sausages, sweet and sour pork, nuggets, neobiani, etc. Examples of noodles comprise sealed and packed fresh noodles. Additionally, the composition may be used for manufacturing retort foods, soups, etc.

As used herein, the term "functional food", which has the same meaning as the term "for special health use (FoSHU)", refers to a food with high effects in medicinal and medical treatment, modulating so as to efficiently exhibit a body modulating function as well as provide nutrients. The functional food may be manufactured in various forms including tablets, capsules, powders, granules, liquids, pills, etc., in order to obtain useful effects for the prevention or amelioration of inflammatory bowel diseases.

In a further aspect of the present invention to achieve the objectives, there is provided a method for inhibiting the expression of inflammatory cytokines including treating the tissues or cells having overexpression of inflammatory cytokines with the pharmaceutical composition of the present invention.

As used herein, the term "inflammatory cytokines" refers to cytokines which induce inflammatory reactions in the body, and the inflammatory cytokines may include IL-1β, TNF-α, IL-6, MCP-1, etc., although not limited thereto.

According to an embodiment of the present invention, inflammatory bowel diseases occurred in mice exposed to cigarette smoke, thus increasing the expression levels of inflammatory cytokines such as TNF-α, IL-6 and IL-1β. However, when the mice were administered with the pharmaceutical composition of the present invention, the increase in the expression levels of inflammatory cytokines such as TNF-α, IL-6 and IL-1β was inhibited (FIGS. 4A through 4C). Additionally, the mRNA level of MMP12, which is known to destroy elastin and collagen, was shown to have the same pattern (FIG. 4D).

Hereinafter, the present invention will be explained in greater detail through the following examples as set forth herein below, but they are disclosed for illustrative purposes only and are not to be construed as limiting the scope of the present invention.

Example 1: Effect of a Stemonae Radix Extract on Cell Line

Example 1-1: Preparation of Materials

First, dried powder of a Stemonae Radix hot-water extract purchased from SUN TEN (Taipei, Taiwan) was dissolved in water, and filtered to obtain a liquid extract of Stemonae Radix (extract of root of *Stemona japonica* Miguel, ERSJM).

Meanwhile, the RAW 264.7 cell line purchased from the Korean Cell Line Bank (KCLB) was inoculated into a DMEM medium (10% FBS, 1% physiological saline), and cultured in an incubator with 5% $CO_2$ maintained at 37° C.

Example 1-2: Evaluation of Cell Toxicities of Stemonae Radix Extract

The RAW 264.7 cell line cultured in Example 1 was aliquoted into a 96-well plate at a concentration of $2 \times 10^5$ cells/well, added to a DMEM medium, and cultured in an incubator with 5% $CO_2$ maintained at 37° C. Then, the medium was removed from the cultured cells, replenished with a DMEM medium containing Stemonae Radix extracts at concentrations of 0, 1, 10 or 100 μg/mL without FBS, and recultured in an incubator with 5% $CO_2$ maintained at 37° C. for 24 hours. Upon completion of culturing, 50 μL of MTT sol. (2 mg/mL) was added to each well, allowed to react in an incubator with 5% $CO_2$ maintained at 37° C. for 4 hours, the medium was removed from each well, added with 200 μL of DMSO, and their respective absorbance was measured using an ELISA reader. The thus-obtained absorbance was compared to evaluate the cell toxicities of the Stemonae Radix extracts (FIG. 1).

FIG. 1 is a graph illustrating the evaluation result of cell toxicities of Stemonae Radix extracts. As illustrated in FIG.

1, no cell toxicities were observed even when treated with a high concentration of the Stemonae Radix extract (extract of root of *Stemona japonica* Miguel, ERSJM). Therefore, it was confirmed that the Stemonae Radix extract is a safe material without cell toxicity.

Example 1-3: Effect of Stemonae Radix Extract on Nitric Oxide (NO) Production

It is known that the concentration of nitric oxide (NO) in the blood plasma of patients with inflammatory bowel diseases such as Crohn's disease and ulcerative colitis is significantly increased. In this regard, the effect of the Stemonae Radix extract on the cell line, wherein the NO production was artificially increased by LPS treatment, was examined.

Specifically, the RAW 264.7 cell line cultured in Example 1 was aliquoted into a 24-well plate at a concentration of $1 \times 10^6$ cells/well, added with a DMEM medium, and cultured in an incubator with 5% $CO_2$ maintained at 37° C. Then, the medium was removed from the cultured cells, replenished with a DMEM medium containing Stemonae Radix extracts at concentrations of 0, 1, 10 or 100 μg/mL without FBS, respectively, and recultured in an incubator with 5% $CO_2$ maintained at 37° C. In two hours, LPS was added to each well to a final concentration of 1 μg/mL and cultured for 24 hours. Upon completion of culturing, supernatants were collected from each well, and a Griess reagent was added thereto. The level of the resulting NO production in each cell was measured, compared, and the effect of the Stemonae Radix extract on NO production was evaluated (FIG. 2). In particular, the cell line used as the control group was not treated with anything, whereas the cell line used as the comparative group was treated with only LPS without treating with the Stemonae Radix extract.

FIG. 2 is a graph illustrating the evaluation result of the effect of Stemonae Radix extracts on NO production. As illustrated in FIG. 2, the level of NO was rapidly increased in the comparative group (lps), which was treated with LPS, compared to that of the control group (con), but the level of NO decreased with the increase of the treatment concentration of the Stemonae Radix extract (ERSJM).

Accordingly, it was confirmed that the Stemonae Radix extract has an inhibitory effect on cell damage due to NO production.

Example 1-4: Effect of Stemonae Radix Extract on Production of Inflammatory Cytokines The effect of the Stemonae Radix extract on the levels of inflammatory cytokines (INF-α, IL-1β, IL-6 or MCP-1) produced in the respective RAW 264.7 cell line treated with LPS prepared in Example 1-3 was examined.

First, the respective antibodies corresponding to each of the inflammatory cytokines (INF-α, IL-6, IL-1β or MCP-1) were coated on the substrates of an ELISA kit and kept at 4° C. overnight. Then, each of the substrates was blocked by adding an assay diluent thereonto, and treated with the culture supernatants obtained from each of the RAW 264.7 cell lines treated with LPS prepared in Example 1-3, had detection antibodies of the ELISA kit added, and had the TMB solution of the ELISA kit added to induce a color reaction. Then, the absorbance of the resulting substrates was measured by applying it to an ELISA reader and compared with each other (FIGS. 3A through 3D).

FIG. 3A is a graph illustrating the evaluation result of the effect of Stemonae Radix extracts on TNF-α production; FIG. 3B is a graph illustrating the evaluation result of the effect of Stemonae Radix extracts on IL-1β production; FIG. 3C is a graph illustrating the evaluation result of the effect of Stemonae Radix extracts on IL-6 production; and FIG. 3D is a graph illustrating the evaluation result of the effect of Stemonae Radix extracts on MCP-1 production.

As illustrated in FIGS. 3A through 3D, in the RAW 264.7 cell line, the levels of inflammatory cytokines were rapidly increased in the comparative group (lps), which was treated with LPS, compared to that of the control group (con), but the levels of all inflammatory cytokines decreased along with the increase of the treatment concentration of the Stemonae Radix extract (ERSJM).

Accordingly, it was confirmed that the Stemonae Radix extract has an inhibitory effect on the production of inflammatory cytokines.

Example 2: Effect of Stemonae Radix Extract on Mice

Example 2-1: Induction of Inflammation Bowel Diseases (IBD) by Treatment with Cigarette Smoke Cigarettes are known to induce inflammatory bowel diseases (IBD) (Gareth A O Thomas, et al., Postgrad. Med. J., 76(895):273-279, 2000 May) and thus mice were exposed to cigarette smoke to induce inflammatory bowel diseases in the mice.

First, six-week old female C57BL/6 mice with body weight ranging from 20 g to 25 g were given ad libitum access to food and water, the breeding room was set to a temperature from 21° C. to 24° C. with a humidity of 40% to 60%, and the light-dark cycle was controlled at 12 hour intervals.

The thus-bred mice were orally administered with the liquid extract of Stemonae Radix obtained in Example 1-1 at a dose of 100 mg/kg, placed into a smoking chamber, exposed to cigarette smoke by the smoking of 3 reference cigarettes 3R4F (University of Kentucky, Lexington, Ky.) for 30 minutes, placed therein for 30 minutes after removing the cigarette smoke therefrom, the cigarette smoke treatment process was repeated 4 times, and the entire cigarette smoke treatment process was performed once daily five times per week for a period of three weeks, thereby inducing inflammatory bowel diseases (IBD) in the mice and using them as the experimental group. In particular, the mice not treated with cigarette smoke were used as a control group (CON), the mice exposed to cigarette smoke but not treated with the liquid extract of Stemonae Radix were used as a comparative group (CS), and the number of mice assigned in each group was three for the control group and the comparative group, respectively, and two mice for the experimental group (ERSJM).

Example 2-2: Comparison of Expression Levels of Inflammatory Cytokines and MMP12

First, the mice in the control group, the comparative group, and the experimental group obtained in Example 2 were sacrificed and colorectal tissues were collected from the mice of each group. Total RNA was obtained from the thus-collected colorectal tissues using the RNeasy Mini kit (QIAGEN, USA). Specifically, each of the colorectal tissues was added with 600 μL of RLT buffer solution to destroy cells, further added with 600 μL of 70% ethanol, and mixed. After adding 700 μL of the mixture into an RNeasy mini column of the RNeasy Mini kit and centrifuging it at 8,000×g for 15 seconds, the residual solution was added with 700 μL of RW1 buffer included in the above kit, centrifuged at 8,000×g for 15 seconds, and the residual solution was collected. Then, 500 μL of RPE buffer solution included in the above kit was added to the residual solution, centrifuged at 8,000×g for 15 seconds, and the residual solution was collected. 50 μL of RNase free water was added to the resulting residual solution was added with, centrifuged at 8,000×g for 1 minute to finally obtain the total RNA. The thus-obtained total RNA was quantitated via spectrophotometer (ND-1000, NanoDrop Technologies Inc. USA), electrophoresed on a 1% agarose gel, and stained with ethidium-bromide (Et-Br, Sigma-Aldrich, USA) for evaluating its state.

Meanwhile, the thus-obtained total RNA was analyzed via real-time RT-PCR. For the above analysis, cDNA was obtained via RT-PCR (95° C.: 15 sec and 60° C.: 1 min, 40 cycles) using 2 μg of the thus-obtained total RNA, SYBR Green I Master Mix (Applied Biosystems, Foster City, Calif., USA) and primers (Genotech Inc., Korea). A real-time PCR was performed by applying the thus-obtained cDNA to the Applied Biosystems 7300 Real time PCR System, and the mRNA levels of MMP12, which is known to destroy inflammatory cytokines such as IL-6, TNF-α, and IL-1β, and elastin and collagen, of the mice in the control group, the comparative group, and the experimental group were compared (FIGS. 4A through 4D).

FIG. 4A is a graph illustrating the change in the level of IL-6 mRNA by the treatment of a Stemonae Radix extract of the present invention; FIG. 4B is a graph illustrating the change in the level of TNF-α mRNA by the treatment of a Stemonae Radix extract of the present invention; FIG. 4C is a graph illustrating the change in the level of IL-1β mRNA by the treatment of a Stemonae Radix extract of the present invention; and FIG. 4D is a graph illustrating the change in the level of MMP12 mRNA by the treatment of a Stemonae Radix extract of the present invention.

As illustrated in FIGS. 4A through 4D, the control group (CON) not treated with cigarette smoke showed low mRNA levels of IL-6, TNF-α, IL-1β and MMP12, whereas the comparative group (CS) treated with only cigarette smoke showed a drastic increase in the mRNA levels of IL-6, TNF-α, IL-1β and MMP12, and the experimental group, administered with the Stemonae Radix extract (ERSJM) prior to their exposure to cigarette smoke, showed inhibitions of the increase in mRNA levels of IL-6, TNF-α, IL-1β and MMP12 induced by cigarette smoke.

From the foregoing, it was confirmed that the Stemonae Radix extract provided in the present invention has an inhibitory effect on the occurrence of inflammatory bowel diseases due to cigarette smoke.

Example 2-3: Comparison of Total Number of Lactobacilli

It is known that the occurrence of an inflammatory bowel disease can reduce the number of intestinal microorganisms. In this regard, the effect of the liquid extract of Stemonae Radix on the number of the lactobacilli in the intestine was examined.

First, the mice in the control group, the comparative group, and the experimental group obtained in Example 2 were sacrificed and cecal tissues were collected from the mice of each group. 1 g of the thus-collected cecal tissues and 9 mL of physiological saline were mixed and physically pulverized. The pulverized products were diluted by adding 10 volumes of a physiological saline solution, respectively. 100 μL each of the thus-obtained diluted solutions was spread onto a solid medium for culturing lactobacilli (MRS agar plate), cultured at 37° C. for 48 hours, and the total number of bactobacilli colonies formed on the solid medium was counted and compared (FIG. 5).

FIG. 5 is a graph illustrating the change in the number of lactobacilli following the treatment with a Stemonae Radix extract.

As illustrated in FIG. 5, the control group (CON) not treated with cigarette smoke showed a high number of lactobacilli, whereas the comparative group (CS) treated with only cigarette smoke showed a rapid decrease in the number of lactobacilli, and the experimental group, administered with the Stemonae Radix extract (ERSJM) prior to their exposure to cigarette smoke, showed inhibitions of the decrease in the number of lactobacilli induced by cigarette smoke.

From the foregoing, it was confirmed that the Stemonae Radix extract provided in the present invention has an inhibitory effect on the occurrence of inflammatory bowel diseases due to cigarette smoke, which induce the decrease of the number of lactobacil.

Example 2-4: Comparison of Change in Body Weight

It is known that the animals having an inflammatory bowel disease lose body weight. In this regard, the effect of the liquid extract of Stemonae Radix on the inflammatory bowel diseases from the aspect of body weight change was examined.

That is, the body weight of the mice in the control group, the comparative group, and the experimental group obtained in Example 2-1 was measured on the test start day (day 0) using a precision scale E06120, measured at 2 day intervals thereafter, and compared thereon (FIG. 6).

FIG. 6 is a graph illustrating the change in the body weight of mice with the treatment of a Stemonae Radix extract.

As illustrated in FIG. 6, the control group (CON) not treated with cigarette smoke was shown to maintain high body weight, whereas the comparative group (CS), which was treated with only cigarette smoke and thus developed an inflammatory bowel disease, showed a rapid decrease in their body weight, and the experimental group (ERSJM), administered with the Stemonae Radix extract prior to their exposure to cigarette smoke, showed inhibitions of the decrease of body weight induced by cigarette smoke.

From the foregoing, it was confirmed that the Stemonae Radix extract of the present invention can inhibit inflammatory bowel diseases caused by cigarette smoke.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating ulcerative colitis or Crohn's disease comprising administering a pharmaceutically effective amount of a pharmaceutical composition to a subject having the ulcerative colitis or Crohn's disease, wherein the pharmaceutical composition comprises a Stemonae Radix extract.

2. The method of claim 1, wherein the Stemonae Radix extract is a water extract of the Stemonae Radix.

3. The method of claim 1, wherein the pharmaceutical composition further comprises a pharmaceutically acceptable carrier, excipient, or diluent.

\* \* \* \* \*